(12) United States Patent
Eskildsen et al.

(10) Patent No.: US 12,061,082 B2
(45) Date of Patent: Aug. 13, 2024

(54) CALIBRATION METHOD AND DEVICE FOR CARRYING IT OUT

(71) Applicant: Amfitech ApS, Tørring (DK)

(72) Inventors: Jørn Eskildsen, Tørring (DK); Lau Kofoed Kierstein, Vejle (DK)

(73) Assignee: Amfitech ApS, Tørring (DK)

( * ) Notice: Subject to any disclaimer, the term of this patent is extended or adjusted under 35 U.S.C. 154(b) by 240 days.

(21) Appl. No.: 17/374,151

(22) Filed: Jul. 13, 2021

(65) Prior Publication Data

US 2021/0341279 A1 Nov. 4, 2021

Related U.S. Application Data

(63) Continuation of application No. PCT/DK2019/050367, filed on Nov. 27, 2019.

(30) Foreign Application Priority Data

Jan. 15, 2019 (DK) .......................... PA 2019 00051

(51) Int. Cl.
*G01B 7/00* (2006.01)
*G01B 7/30* (2006.01)

(52) U.S. Cl.
CPC .............. *G01B 7/003* (2013.01); *G01B 7/30* (2013.01)

(58) Field of Classification Search
CPC ............................................. A61B 2034/2051
See application file for complete search history.

(56) References Cited

U.S. PATENT DOCUMENTS

| | | | |
|---|---|---|---|
| 6,122,538 A | 9/2000 | Sliwa, Jr. et al. | |
| 2003/0184285 A1* | 10/2003 | Anderson | A61B 34/20 606/1 |
| 2005/0062469 A1* | 3/2005 | Anderson | G01V 3/104 324/207.17 |
| 2008/0174304 A1 | 7/2008 | Anderson | |
| 2008/0186018 A1 | 8/2008 | Anderson | |
| 2010/0271012 A1* | 10/2010 | Patterson | G01B 7/003 324/207.15 |
| 2012/0105362 A1* | 5/2012 | Kremin | G06F 3/0446 345/174 |

(Continued)

FOREIGN PATENT DOCUMENTS

| | | |
|---|---|---|
| EP | 1887309 B1 | 7/2016 |
| EP | 3376264 A1 | 9/2018 |

(Continued)

*Primary Examiner* — Eman A Alkafawi
*Assistant Examiner* — Suresh K Rajaputra
(74) *Attorney, Agent, or Firm* — Elevated IP, LLC

(57) ABSTRACT

Electromagnetic tracking systems and methods for automatically providing the required additional information needed to identify the orientation of a sensor are disclosed. The tracking systems are configured to carry out a digital modulation process to determine one or more parameters needed for calibration and to determine if the carrier wave and the modulated signal are in-phase or 180° out-of-phase at time T=0, thereby determining the operational sign of the carrier wave and thus the orientation of the one or more sensors. In some embodiments, at least one offset coil is arranged to generate an additional magnetic field, and the tracking system may be calibrated on the basis of the additional magnetic field.

20 Claims, 6 Drawing Sheets

(56) References Cited

U.S. PATENT DOCUMENTS

2014/0051983 A1* 2/2014 Schroeder .............. A61B 34/20
                                                                600/424
2017/0238996 A1    8/2017 Frame et al.
2018/0178753 A1*  6/2018 Ette ...................... H04B 17/104
2019/0226825 A1*  7/2019 Schneider .......... G01R 33/0206

FOREIGN PATENT DOCUMENTS

WO       9509562 A1    4/1995
WO    2015155775 A1   10/2015

* cited by examiner

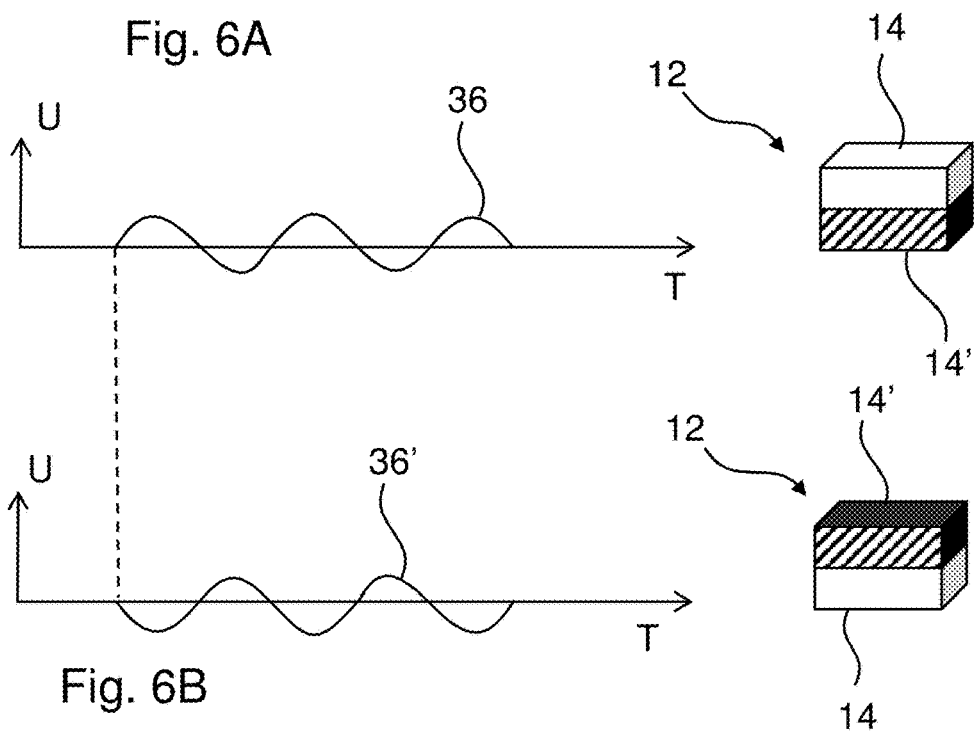
Fig. 6A
Fig. 6B
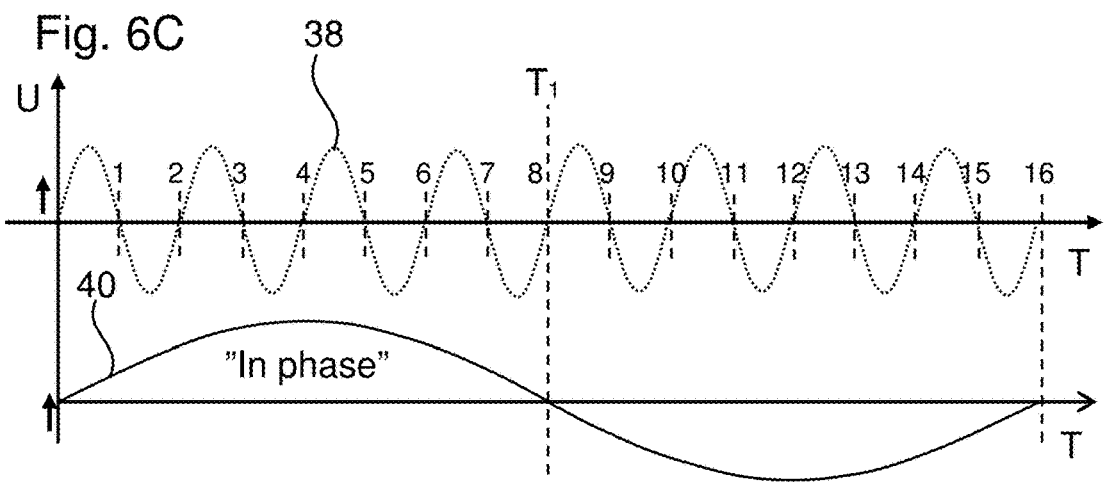
Fig. 6C
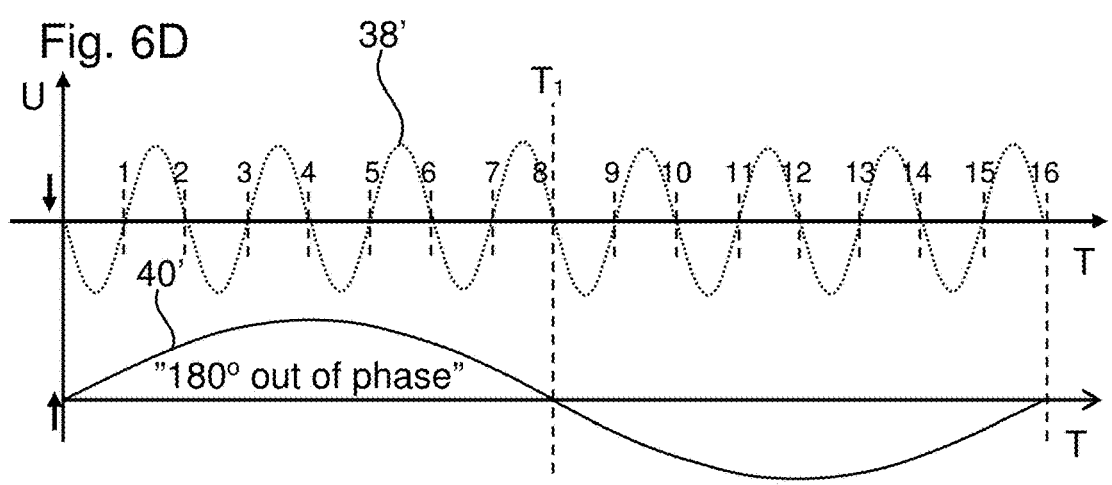
Fig. 6D

CALIBRATION METHOD AND DEVICE FOR CARRYING IT OUT

CROSS REFERENCE TO RELATED APPLICATIONS

This application is a continuation under 35 U.S.C. 111 of International Patent Application No. PCT/DK2019/050367, filed Nov. 27, 2019, which claims the benefit of and priority to Danish Application No. PA 2019 00051, filed Jan. 15, 2019, each of which is hereby incorporated by reference in its entirety.

FIELD OF INVENTION

The present invention relates to a method for automatic calibration of a three-dimensional electromagnetic field tracking system comprising an electromagnetic field transmitter comprising three coils configured to generate three magnetic fields and one or more electromagnetic field receivers each comprising three measurement coils. The invention also relates to a three-dimensional electromagnetic field tracking system comprising means for carrying out such calibration.

BACKGROUND

Recently, there has been increasing development within the field of electromagnetic tracking. An electromagnetic tracking system applies a transmitter (also referred to as a source) to generate a three-dimensional magnetic field. The three-dimensional magnetic field constitutes a reference and is detected and measured by at least one magnetic receiver (also referred to as a sensor). By means of the system comprising the source and the sensor, it is possible to determine the position and orientation of an object.

According to Michael Faraday's Law, when the sensor (which comprises three coils) moves in the space inside an alternating magnetic field, a voltage, proportional to the cross product of the cross-sectional winding area and the intensity of the magnetic field, is induced in every winding thus producing N times the total voltage across the coils (wherein N is the number of turns of the winding). The voltage induced, will immediately make it possible to detect rotation and position relative to the emitter coils of the source.

Electromagnetic tracking systems are used to detect position and orientation in both two-dimensional and three-dimensional systems. The systems are popular because they can dynamically, in real-time measure positions and orientation angles. Accordingly, electromagnetic tracking systems are used in various digital fields including computer-assisted surgery, virtual reality, navigation, ballistic tracking and biomechanics.

Virtual reality systems often apply six-degree-of-freedom electromagnetic tracking systems for determining position and orientation of a sensor (e.g. attached to a user) in the working space. Six-degree-of-freedom electromagnetic tracking systems typically use orthogonal electromagnetic fields to sense three-dimensional position and orientation. The source normally contains three orthogonal coils that are pulsed in a sequence, the receiver (sensor) also has three orthogonal coils configured to measure the electromagnetic field produced by the source. The strength of the received signals is compared to the strength of the sent pulses to determine the position and compared to each other to determine the orientation. Due to noise, additional filtering will normally be required. Generally, the accuracy of the systems decreases as the distance between the source and the sensor increases.

When an electromagnetic tracking system is started, the orientation of the sensor is not known. Accordingly, the electromagnetic field measurements conducted by the sensor provide fewer equations than unknowns and thus the system of linear equations is underdetermined.

Accordingly, the relevant equations have several solutions and it is required to establish within which domain (e.g. hemisphere, quadrant or octant) the sensor is operated. However, many electromagnetic tracking systems cannot automatically identify said domain and thus they cannot distinguish between measurements representing two opposite hemispheres. Normally, the tracker coordinates are reported in a right-handed coordinate system. It has to be specified in which hemisphere the system has to be operated. If the wrong hemisphere is specified a left-handed coordinate system will be used. Accordingly, this fundamental problem referred to as hemisphere disambiguation must be addressed by any electromagnetic tracking system that determines a unique position from various measured parameters (e.g. induced voltages indicative of the strength of the magnetic field). In the prior art this is a major essential challenge.

Therefore, during the initial state the electromagnetic tracking system is required to provide additional information to identify the orientation of the sensor. In the prior art, this is done by arranging the sensor in a predefined position and orientation relative to the source. When the electromagnetic tracking system is started, knowing the predefined position and orientation will be sufficient to provide the additional information required to uniquely identify the orientation of the sensor.

This procedure needs to be repeated when the sensor is moved outside of the range (too far away from the source) or if the system has been shut off. Accordingly, the procedure is a major disadvantage.

US 2008/0174304 A1 discloses an electromagnetic coil arrangement comprising a plurality of electromagnetic sensors located about the periphery of a region and at least one center electromagnetic sensor located at or near the center of the region. The electromagnetic sensors and the at least one center electromagnetic sensor are located in a single plane. The system is configured to be used for tracking an object, e.g. instruments for use in surgery or other medical treatments carried out in a three-dimensional electromagnetic field. This solution, however, does not provide additional information needed to identify the orientation of the sensor.

US 2017/0238996 A1 discloses an electromagnetic coil assembly for a surgical navigation tracking system, however the solution is complex and not easy to use.

Therefore, it would be an advantage to reduce or even eliminate the above-mentioned disadvantages of the prior art.

SUMMARY

It is an object of the invention to provide an electromagnetic tracking system that automatically provides the required additional information needed to identify the orientation of the sensor.

It is also an object of the invention to provide a method for automatically providing the required additional information needed to identify the orientation of the sensor in an electromagnetic tracking system.

In an aspect, a system according to the invention is a three-dimensional alternating current electromagnetic field tracking system for determining the position and orientation of an object, wherein the system comprises: an electromagnetic field transmitter (source) comprising three coils configured to generate three magnetic fields and one or more electromagnetic field receivers (sensors) each comprising three measurement coils, and a control unit, wherein the tracking system is configured to carry out a digital modulation process and thereby determine one or more parameters needed to accomplish the calibration process by means of said digital modulation process, wherein the digital modulation process is a phase-shift keying (PSK) modulation process modulating the phase of a constant frequency carrier wave, wherein the system is configured to determine if the carrier wave and the modulated signal are in phase or 180° out of phase at time T=0 and thereby determine the operational sign of the carrier wave and thus the orientation of the one or more sensors.

In an embodiment, the electromagnetic field transmitter (source) comprises at least one offset coil arranged to generate an additional magnetic field, wherein the offset coil is offset relative to the coils of the electromagnetic field transmitter (source), wherein the control unit is configured to calibrate the system on the basis of the additional magnetic field.

In an embodiment, at least one offset coil comprises a switch (e.g. a transistor) connected to the control unit, wherein the switch is configured to connect and disconnect a first point of the offset coil to a second point of the offset coil, wherein the offset coil is configured to generate the additional magnetic field (by induction) when the first point of the offset coil and the second point are electrically connected to each other by means of the switch and wherein the offset coil is restricted from generating an additional magnetic field (by induction) when the first point of the offset coil and the second point are electrically disconnected from each other by means of the switch.

Hereby, the orientation and/or position of the one or more electromagnetic field receivers (sensors) can be uniquely determined by using the system. Accordingly, the system is self-calibrating and is capable of calibrating itself during start up and when the sensor is moved so far away from the source that the sensor can no longer detect the signals transmitted by the electromagnetic field transmitter (source). Thus, no interference from the user is required and the system therefore provides a user-friendly solution.

The three coils of the electromagnetic field transmitter (source) are usually configured to generate three orthogonal magnetic fields.

In an embodiment, the electromagnetic field transmitter (source) is integrated in a transmitter assembly comprising a housing, wherein the transmitter assembly constitutes a one-piece body.

The system comprises one or more electromagnetic field receivers (sensors) each comprising three measurement coils. The three measurement coils are typically arranged in an orthogonal configuration.

The three coils of each sensor are generally configured to measure three orthogonal magnetic fields. In an embodiment, each sensor is integrated in a sensor assembly comprising a housing, wherein the sensor assembly constitutes a one-piece body.

The control unit may be a separate component.

In an embodiment, the control unit is an integrated part of the electromagnetic field transmitter (source).

The electromagnetic field transmitter (source) comprises at least one offset coil arranged to generate an additional magnetic field. In an embodiment, the additional magnetic field extends parallel to one of the three magnetic fields generated by the coils of the electromagnetic field transmitter (source).

In another embodiment, the additional magnetic field is angled relative to all three magnetic fields generated by the coils of the electromagnetic field transmitter (source).

The offset coil is offset relative to the coils of the electromagnetic field transmitter (source). Hereby, the additional magnetic field will offset the magnetic field generated by the coils of the electromagnetic field transmitter so that turning on the offset coil and turning off the offset coil provides a detectable signal change that can be used to verify the position and orientation of the sensor.

In an embodiment, the offset coil is arranged and configured to generate the additional magnetic field passively by induction. This can be achieved by arranging the offset coil in a magnetic field generated by one of the coils of the electromagnetic field transmitter (source). Accordingly, a counter-electromotive force (back EMF) will be generated in the offset coil when the magnetic field within the coil changes as a function of time. The additional magnetic field will counteract the magnetic field generated by the coil(s) of the electromagnetic field transmitter.

In an embodiment, the offset coil comprises a switch (e.g. a transistor) connected to the control unit, wherein the switch is configured to connect and disconnect a first point of the offset coil to a second point of the offset coil, wherein the offset coil is configured to generate the additional magnetic field (by induction) when the first point of the offset coil and the second point are electrically connected to each other by means of the switch and wherein the offset coil is restricted from generating an additional magnetic field (by induction) when the first point of the offset coil and the second point are electrically disconnected from each other by means of the switch.

In an embodiment, the offset coil is connected to a unit that is configured to deliver an AC current.

The control unit is configured to calibrate the system on the basis of the additional magnetic field. This is done by comparing the measurements made by the one or more sensors with and without the additional magnetic field generated by the offset coil.

In an embodiment, the at least one offset coil is arranged in a configuration in which the additional magnetic field generated by the at least one offset coil extends substantially parallel to one of the three magnetic fields generated by one of the coils of the electromagnetic field transmitter.

In an embodiment, the at least one offset coil extends along a plane extending parallel to one of the coils the electromagnetic field transmitter. Hereby, the additional magnetic field generated by the offset coil will extend parallel to the magnetic field generated by one of the coils of the electromagnetic field transmitter.

In an embodiment, the electromagnetic field transmitter is arranged on a printed circuit board (PCB) and at least one offset coil is integrated in the PCB. Hereby, it is possible to achieve a compact and robust design.

In an embodiment, the electromagnetic field transmitter (source) is arranged on a printed circuit board (PCB) and at least one offset coil extends in a plane perpendicular to the plane of the PCB. Hereby, it is possible to generate a magnetic field parallel to one of the coils of the electromagnetic field transmitter that extends in a plane perpendicular to the plane of the PCB.

In an embodiment, the electromagnetic field transmitter is integrated in a transmitter assembly comprising three coils configured to generate three magnetic fields, wherein one or more offset coils are integrated in the transmitter assembly. In an embodiment, the transmitter assembly may be arranged in a single housing.

It is an advantage that, the tracking system is configured to carry out a digital modulation process and hereby determine one or more parameters needed to accomplish the calibration process by means of said digital modulation process. Hereby, it is possible to provide one or more measurements required to finish the calibration process. This may in particular be an advantage if the source and the sensor are wirelessly connected but not connected by a wired connection.

In an embodiment, the control unit is adapted to carry out a digital modulation process and hereby determine one or more parameters needed to accomplish the calibration process by means of said digital modulation process. Such parameter may be a parameter indicative of the position and/or the orientation of a sensor.

It is an advantage that the digital modulation process is a phase-shift keying (PSK) modulation process. This may be accomplished by modulating the phase of a constant frequency carrier wave (sine or cosine).

In an embodiment, the digital modulation process is an amplitude-shift keying (ASK) modulation process. In this modulation process the amplitude of a carrier wave is varied.

In an embodiment, the digital modulation process is an asymmetric phase-shift keying (APSK) modulation process. In this process both the amplitude and the phase of a carrier wave is modulated.

In an embodiment, the digital modulation process is a frequency-shift keying (FSK) modulation process. The modulation process includes the frequency change of a carrier signal.

In an embodiment, the digital modulation process is a spread spectrum modulation process such as chirp spread spectrum (CSS) and/or direct-sequence spread spectrum (DSSS) modulation process.

In an embodiment, the tracking system comprises an electronic oscillator circuit (clock generator) configured to generate a timing signal (clock signal) for use in synchronizing one or more circuits' operation.

In an embodiment, the clock generator comprises a resonant circuit and an amplifier. In an embodiment, the resonant circuit is a quartz piezo-electric oscillator. It may be beneficial that the amplifier is configured to invert signals from the oscillator and feed a portion back into the oscillator in order to maintain the oscillation frequency.

In an embodiment, the generator comprises a modifying section configured to modify the base signal. The modifying section may comprise a frequency divider or clock multiplier sections. In an embodiment, the clock generator is programmable so that the number used in the frequency divider or clock multiplier can be changed.

In an embodiment, the tracking system comprises a voltage-controlled crystal oscillator configured to provide a timing signal to synchronize one or more operations.

In an embodiment, the tracking system comprises a voltage-controlled crystal oscillator clock generator. The voltage-controlled crystal oscillator can be used for fine adjustment of the operating frequency.

By using a voltage-controlled oscillator it is possible to frequency drift (change in accuracy of a given frequency over environmental changes such as temperature, humidity, or pressure, or simply over long periods of time). It is an advantage to apply a voltage-controlled oscillator because frequency drift is an unintended and generally arbitrary offset of the oscillator from its nominal frequency.

In an embodiment, the tracking system comprises a varicap diode arranged in parallel with a capacitor.

A method according to the invention is a method for automatic calibration of a three-dimensional alternating current electromagnetic field tracking system comprising:
  an electromagnetic field transmitter comprising three coils configured to generate three magnetic fields and
  one or more electromagnetic field receivers each comprising three measurement coils and
  a control unit,
wherein the method comprises the following steps:
  carrying out a digital modulation process and hereby determining one or more parameters needed to accomplish the calibration process by means of said digital modulation process, wherein the digital modulation process is a phase-shift keying (PSK) modulation process modulating the phase of a constant frequency carrier wave;
  determining if the carrier wave and the modulated signal are in phase or 180° out of phase at time T=0 and hereby determining the operational sign of the carrier wave and thus the orientation of the one or more sensors.

Hereby, the orientation and/or position of the one or more electromagnetic field receivers (sensors) can be uniquely determined using the method. Accordingly, the method eliminates the need of interference from the user during calibration of the tracking system.

In an embodiment, the method comprises the following steps:
  generating an additional magnetic field by means of an offset coil being offset relative to the coils of the electromagnetic field transmitter and
  calibrating the system on the basis of the additional magnetic field.

In an embodiment, the additional magnetic field is generated using at least one offset coil that is arranged in a configuration in which the additional magnetic field generated by the at least one offset coil extends parallel to one of the three magnetic fields generated by one of the coils of the electromagnetic field transmitter.

In an embodiment, the method comprises the following steps:
  generating an additional magnetic field by means of an offset coil being offset relative to the coils of the electromagnetic field transmitter and
  calibrating the system on the basis of the additional magnetic field, wherein the offset coil is arranged and configured to generate the additional magnetic field passively by induction.

In an embodiment, the method comprises the step of turning on and off a switch in order to bring the offset coil into a first mode, in which the offset coil is configured to generate the additional magnetic field and a second mode, in which the offset coil does not generate an additional magnetic field.

In an embodiment, the offset coil comprises a switch (e.g. a transistor) connected to the control unit, wherein the switch is configured to connect and disconnect a first point of the offset coil to a second point of the offset coil, wherein the offset coil is configured to generate the additional magnetic field (by induction) when the first point of the offset coil and the second point are electrically connected to each other by means of the switch and wherein the offset coil is restricted from generating an additional magnetic field (by induction) when the first point of the offset coil and the second point are electrically disconnected from each other by means of the switch.

In an embodiment, the additional magnetic field is generated using at least one offset coil that extends along a plane extending parallel to one of the coils of the electromagnetic field transmitter. Hereby, the additional magnetic field generated by an offset coil will only cause a change in the magnetic field in one of the three coils of the source.

In an embodiment, the additional magnetic field is generated using at least one offset coil arranged and configured to generate the additional magnetic field passively by induction. This can be achieved by arranging the offset coil in a magnetic field generated by one of the coils of the electromagnetic field transmitter (source). Accordingly, a counter-electromotive force (back EMF) will be generated in the offset coil when the magnetic field within the coil changes as a function of time. The additional magnetic field will counteract the magnetic field generated by the coil(s) of the electromagnetic field transmitter.

In an embodiment, the additional magnetic field is generated using at least one offset coil comprising a switch (e.g. a transistor) connected to the control unit, wherein the switch is configured to connect and disconnect a first point of the offset coil to a second point of the offset coil, wherein the offset coil is configured to generate the additional magnetic field (by induction) when the first point of the offset coil and the second point are electrically connected to each other by means of the switch and wherein the offset coil is restricted from generating an additional magnetic field (by induction) when the first point of the offset coil and the second point are electrically disconnected from each other by means of the switch.

In an embodiment, the additional magnetic field is generated using at least one offset coil connected to a unit that is configured to deliver an AC current.

It is an advantage that, the method comprises the step of carrying out a digital modulation process, thereby determining one or more parameters needed to accomplish the calibration process by means of said digital modulation process. Hereby, it is possible to provide one or more measurements required to finish the calibration process. This may in particular be an advantage if the source and the sensor are wirelessly connected but not connected by a wired connection.

It is an advantage that the modulation process of the method is a phase-shift keying (PSK) modulation process.

In an embodiment, the modulation process is an amplitude-shift keying (ASK) modulation process.

In an embodiment, the modulation process of the method is an asymmetric phase-shift keying (APSK) modulation process.

In an embodiment, the modulation process of the method is a frequency-shift keying (FSK) modulation process.

In an embodiment, the modulation process of the method is a spread spectrum modulation process such as chirp spread spectrum (CSS) and/or direct-sequence spread spectrum (DSSS) modulation process.

In an embodiment, the method is carried out using a control unit integrated in the electromagnetic field transmitter.

DESCRIPTION OF THE DRAWINGS

The invention will become more fully understood from the detailed description given herein below. The accompanying drawings are given by way of illustration only, and thus, they are not limitative of the present invention. In the accompanying drawings:

FIG. 6A shows a graph illustrating voltage as a function of time, wherein a sensor is arranged in a first configuration;

FIG. 6B shows a graph illustrating voltage as a function of time, wherein a sensor is arranged in a second configuration;

FIG. 6C shows how phase-shift keying (PSK) is used to gain additional information for carrying out the method according to the invention and FIG. 6D shows how phase-shift keying (PSK) is used to gain additional information for carrying out the method according to the invention.

DETAILED DESCRIPTION OF THE INVENTION

Figure 1A:
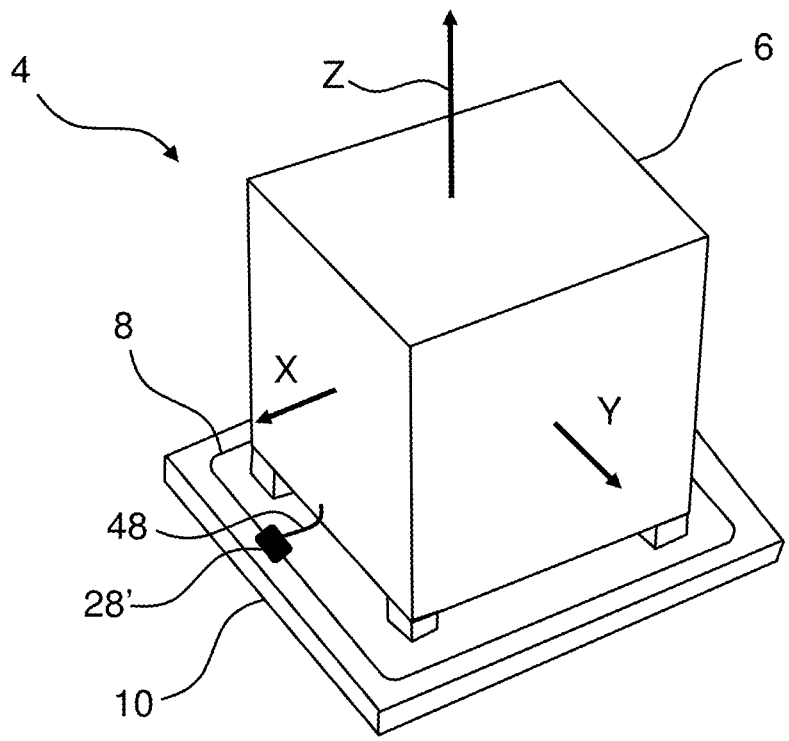
FIG. 1A shows a schematic, perspective top view of an electromagnetic field transmitter of an electromagnetic tracking system according to the invention.

Referring now in detail to the drawings for the purpose of illustrating preferred embodiments of the present invention, an electromagnetic field transmitter of an electromagnetic tracking system of the present invention is illustrated in FIG. 1A.

FIG. 1A illustrates a schematic, perspective top view of an electromagnetic field transmitter (source) 4 of an electromagnetic tracking system according to the invention. The source 4 comprises a coil assembly 6 comprising three orthogonal coils wound on a cubic core (not shown). The coils extend perpendicular to the X-axis, the Y-axis and the Z-axis of the source 4, respectively. The coil assembly 6 is arranged on and electrically connected to a PCB 10. An offset coil 8 is provided at the PCB 10. The offset coil 8 extends along and in a close distance from the outer periphery of the PCB 10. The offset coil 8 extends parallel with the PCB 10 and with one of the three orthogonal coils of the coil assembly 6.

A switch 28' formed as a transistor is connected to a first point of the offset coil 8 and to a second point of the offset coil 8. The transistor 28' is electrically connected to a control unit (not shown) by a connector 48. Accordingly, the control unit can connect and disconnect the offset coil 8 when the offset coil 8 is connected by means of the transistor 28'.

The offset coil 8 is arranged and configured to generate the additional magnetic field passively by induction. The additional magnetic field is generated by the offset coil 8 by induction when a time varying magnetic field is generated by one of the coils of the electromagnetic field transmitter (source) 4.

The transistor 28' is configured to connect and disconnect the first point of the offset coil 8 to a second point of the offset coil 8, wherein the offset coil 8 is configured to generate the additional magnetic field (by induction) when the first point of the offset coil 8 and the second point are electrically connected to each other by means of the transistor 28' and wherein the offset coil 8 is restricted from generating an additional magnetic field (by induction) when the first point of the offset coil 8 and the second point of the offset coil 8 are electrically disconnected from each other by means of the transistor 28'.

Figure 1B:
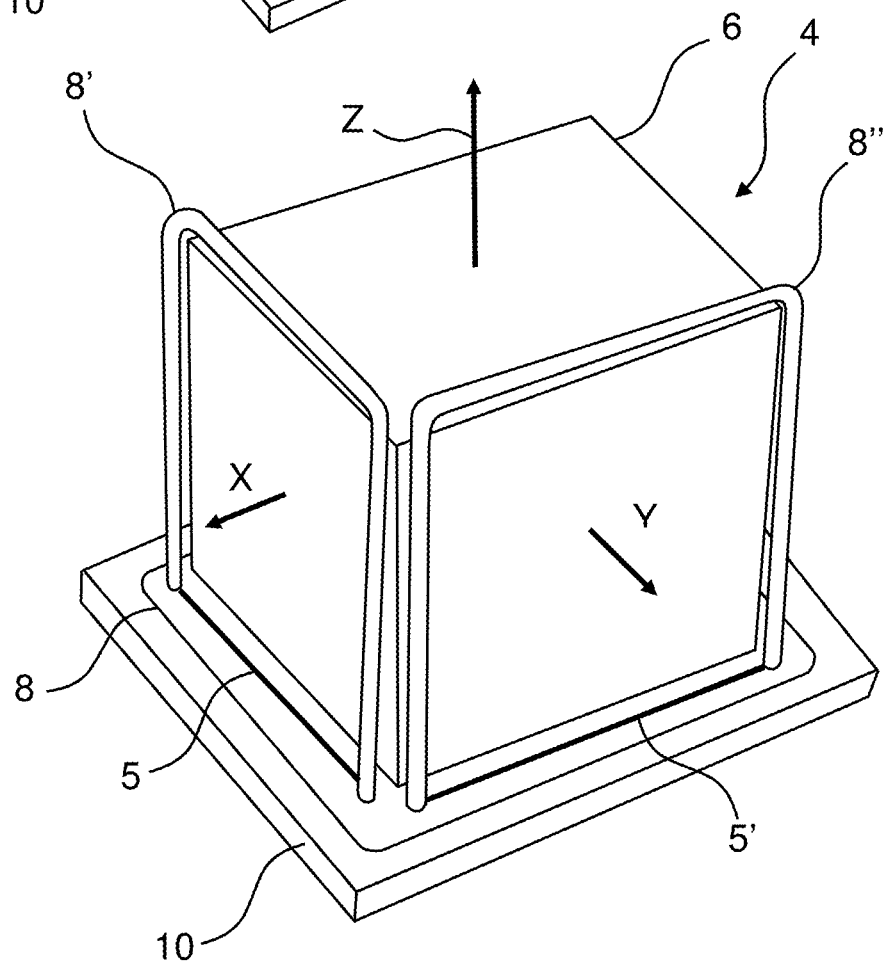
FIG. 1B shows a schematic, perspective top view of another electromagnetic field transmitter of an electromagnetic tracking system according to the invention.

FIG. 1B illustrates a schematic, perspective top view of another electromagnetic field transmitter (source) 4 of an electromagnetic tracking system according to the invention. The source 4 comprises a coil assembly 6 that is arranged on and electrically connected to a PCB 10 like the ones shown in FIG. 1A. A first offset coil 8 extends along the outer periphery of the PCB 10 and perpendicular to the Z-axis. Accordingly, the first offset coil 8 is configured to generate a magnetic field extending parallel to the Z-axis.

The source 4 comprises a second offset coil 8' having a U-shaped portion extending perpendicular to the first offset coil 8 and the PCB 10. A portion 5 of the second offset coil 8' extends along the PCB 10 and connects the free ends of the U-shaped portion of the second offset coil 8'. The second offset coil 8' is configured to generate a magnetic field extending parallel to the X-axis.

The source 4 comprises a third offset coil 8'' having a U-shaped portion extending perpendicular to the first offset coil 8, the second offset coil 8' and the PCB 10. A portion 5' of the third offset coil 8' extends along the PCB 10 and connects the free ends of the U-shaped portion of the third offset coil 8''. The third offset coil 8'' is configured to generate a magnetic field extending parallel to the Y-axis.

Therefore, it is possible to generate one, two or three additional magnetic fields by means of one, two or three of the offset coils 8, 8', 8''. The control unit (not shown) of the electromagnetic tracking system can apply these additional magnetic fields to carry out an automatic calibration. When the electromagnetic tracking system is started, the additional information available on the basis of measurements carried out with and without energizing the offset coils 8, 8', 8'' is sufficient to provide information required to uniquely identify the orientation of a sensor (not shown) of the system.

Figure 2A:
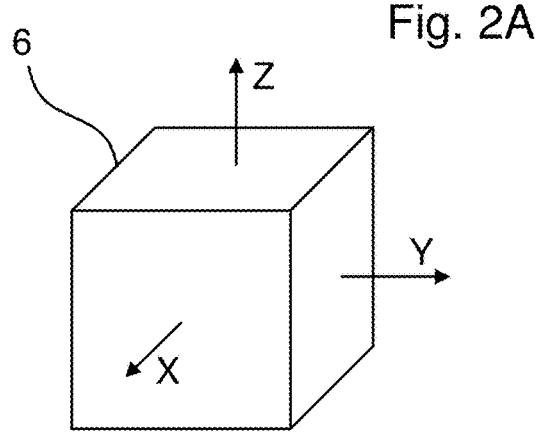
FIG. 2A shows a schematic view of a coil assembly arranged a distance from an electromagnetic field receiver (sensor) according to the invention, wherein the sensor has a first orientation.

FIG. 2A illustrates a schematic view of a coil assembly 6 arranged a distance from an electromagnetic field receiver (sensor) 12 according to the invention, wherein the sensor 12 has a first orientation in which the top portion 14 of the sensor 12 is white and the bottom portion 14' of the sensor 12 is dark.

Figure 2B:
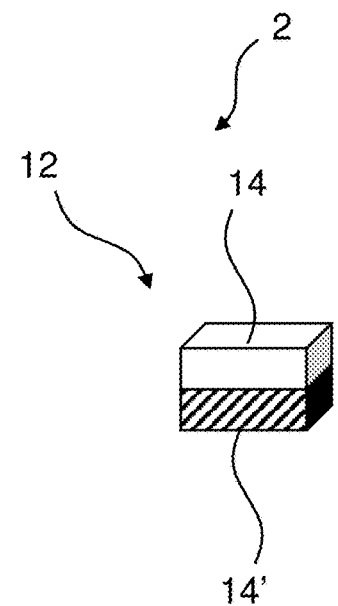
FIG. 2B shows a schematic view of the coil assembly and sensor shown in FIG. 2A, wherein the sensor is orientated differently.
Figure 2B:
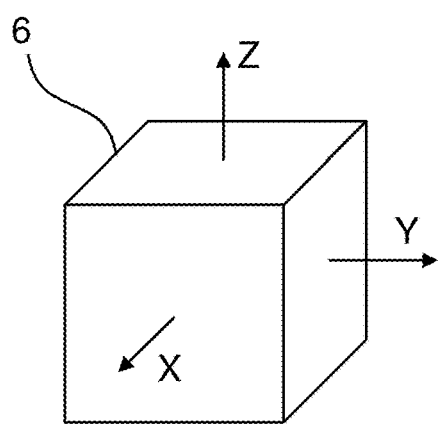

FIG. 2B illustrates a schematic view of the coil assembly 6 shown in FIG. 2A, in a configuration in which the sensor 12 is turned upside down so that the top portion 14 of the sensor 12 is dark and the bottom portion 14' of the sensor 12 is white. Accordingly, the sensor 12 has been rotated 180 degrees with respect to the X-axis or the Y-axis of the coil assembly 6.

Based on the strength of the magnetic field transmitted by the source and detected by the sensor 12, it is possible to uniquely determine the position of the sensor 12. However, the sensor 12 will have the same position in FIG. 2A and in FIG. 2B. Accordingly, by applying an offset coil as explained with reference to FIG. 1A or FIG. 1B, it is possible to apply measurements with and without electrically energizing said offset coil and gain the required information to uniquely determine the orientation of the sensor 12.

In many cases, it would be an advantage to have three orthogonal offset coils arranged and configured to generate additional magnetic fields extending along the X-axis, Y-axis and Z-axis, respectively. Hereby, the electromagnetic tracking system 2 detects the orientation (rotation) of the sensor 12 with respect to any of these axes X, Y, Z. In an embodiment, in which the source and the sensor are connected by wires, a single offset coil may be sufficient to provide the information needed to uniquely determine the orientation and position of the sensor.

Figure 2C:
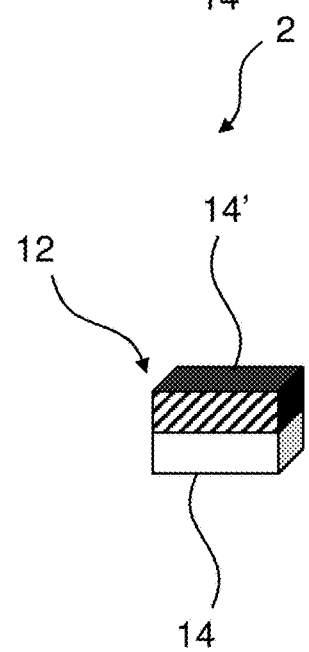
FIG. 2C shows a schematic view of two detected magnetic fields represented as a first vector in a first hemisphere and a second opposite oriented vector in the second hemisphere.
Figure 2C:
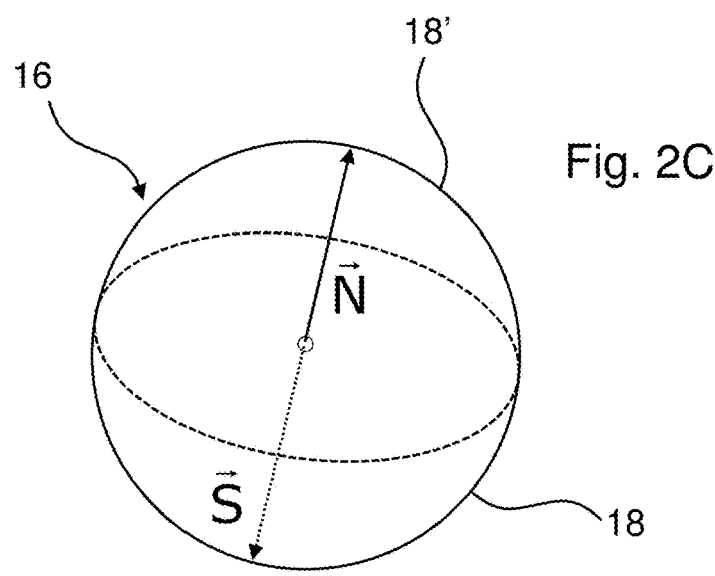

FIG. 2C illustrates a schematic view of two detected magnetic fields represented as a first vector $\vec{N}$ in a first hemisphere 18' and a second opposite oriented vector $\vec{S}$ in the second hemisphere 18. The system and method according to the invention provide the additional information (additional magnetic field) required to determine if a sensor is arranged in either the first hemisphere 18' or the second hemisphere 18.

Figure 3:
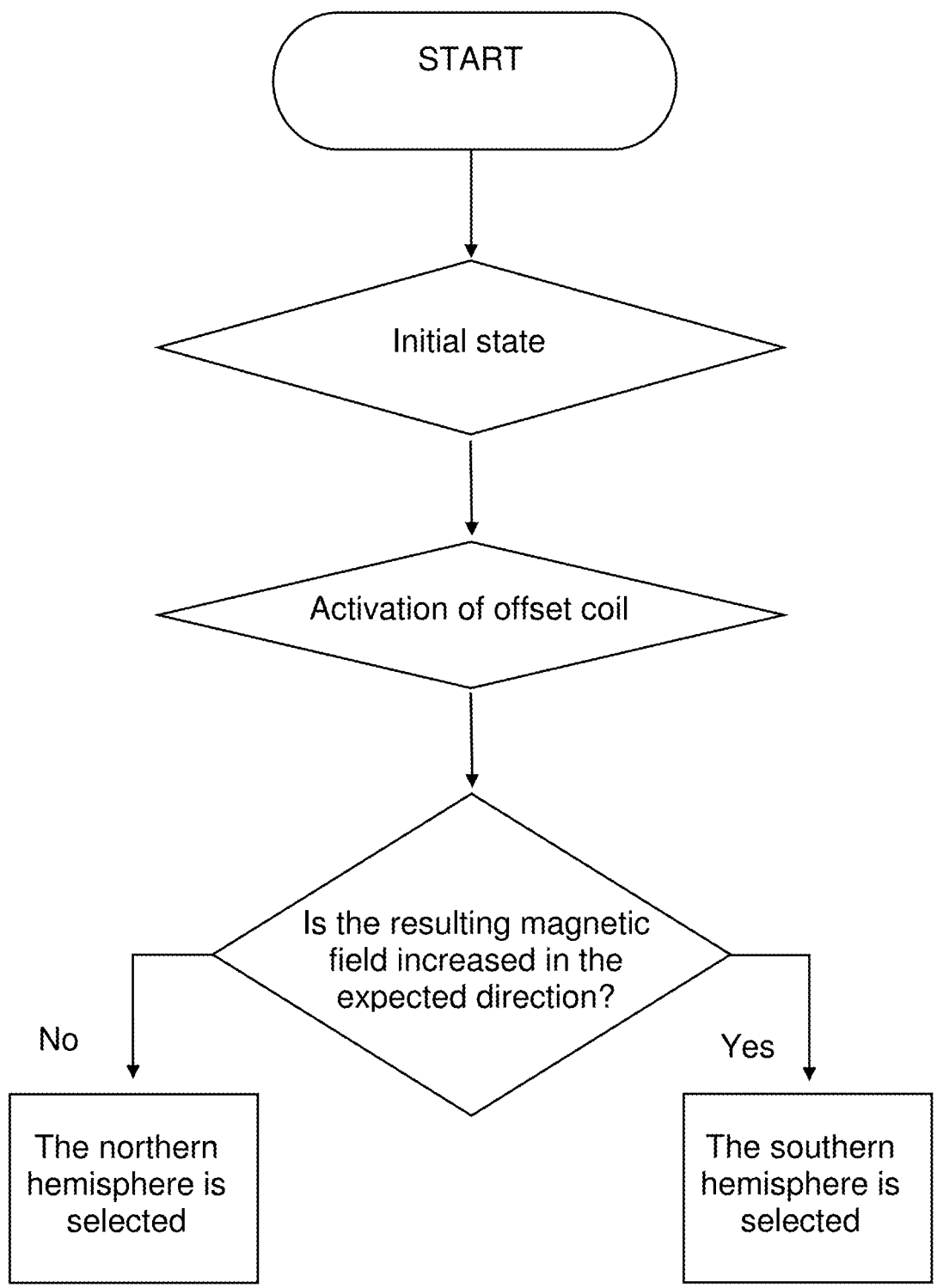
FIG. 3 shows a flow chart illustrating how the correct hemisphere can be selected.

FIG. 3 illustrates a flow chart illustrating how the correct hemisphere can be selected. When the system is started, a second step "Initial state" is carried out. The second step is a step in which initial information e.g. about the operational sign of the carrier signal is provided. This may be done using a digital modulation process, by which it is possible to determine one or more parameters indicative of the position and/or the orientation of a sensor. In one embodiment, the digital modulation process is a PSK modulation process carried out in order to modulate the phase of a constant frequency carrier wave.

Hereafter the offset coil is activated. Hereby, an additional magnetic field is generated by means of the offset coil. It has to be mentioned that several offset coils may be applied to generate several additional magnetic fields. The next step involves verifying if the resulting magnetic field corresponds to the one expected assuming that the sensor is arranged in the southern hemisphere. If this is the case, the southern hemisphere is selected. On the other hand, if this not the case, the northern hemisphere is selected.

Figure 4A:
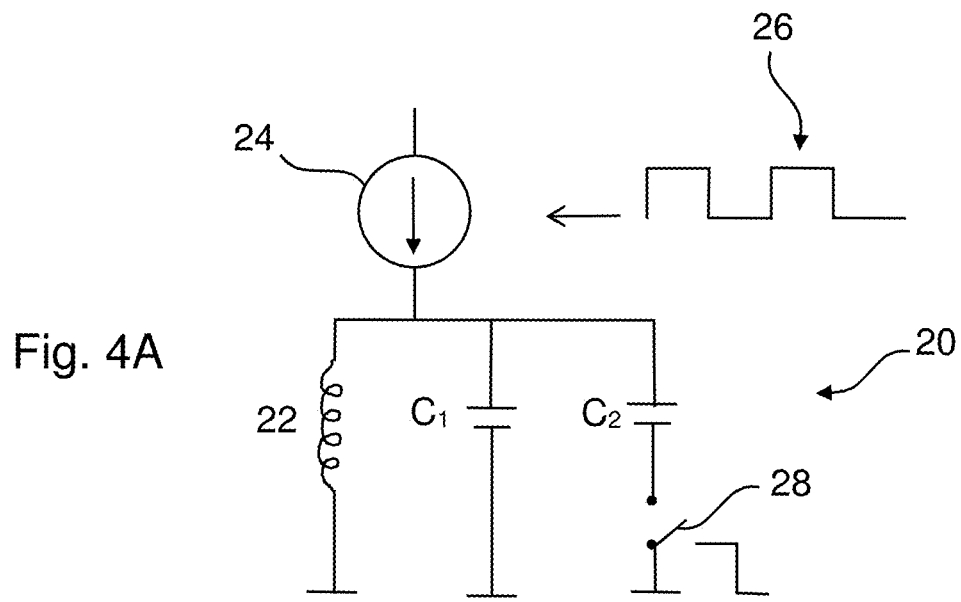
FIG. 4A shows an electric circuit of an electromagnetic tracking system according to the invention.

FIG. 4A illustrates an electric circuit 20 of an electromagnetic tracking system according to the invention. The electric circuit 20 is a LC circuit, configured to be used to carry out a PSK modulation process to modulate the phase of a constant frequency carrier impulse 26. The PSK modulation process is carried out in order to allow an automatic calibration of the system. The electric circuit 20 comprises an inductor coil 22 electrically connected to a first capacitor $C_1$. A second capacitor $C_2$ is connected to the first capacitor $C_1$. A current generator 24 is arranged to supply a pulsed signal 26. Accordingly, the LC circuit 20 is configured to carry out a PSK modulation process and hereby generate signals at a pre-defined frequency (see FIG. 6A and FIG. 6B).

Figure 4B:
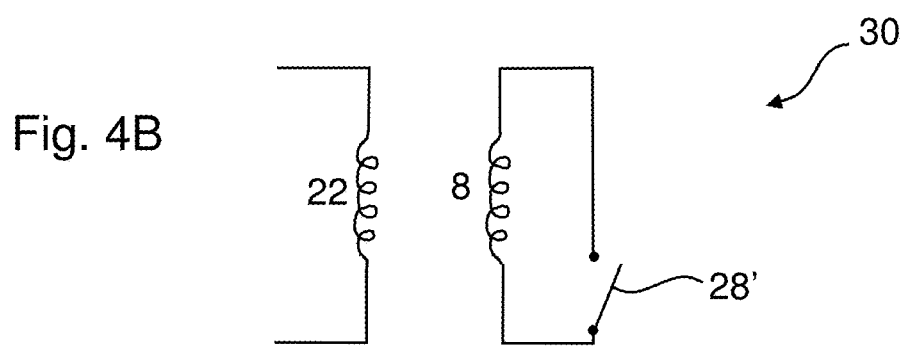
FIG. 4B shows another electric circuit of an electromagnetic tracking system according to the invention.

FIG. 4B illustrates another electric circuit 30 of an electromagnetic tracking system according to the invention. The system corresponds to the one shown in FIG. 1A. The electric circuit 30 comprises a first inductor (a coil of the source of the system) 22 and an offset coil 8 that is arranged to be electrically connected and disconnected by means of a switch 28'. Accordingly, by controlling the switch 28' it is possible to activate and deactivate the offset coil 8. The switch 28' may be controlled using a processor (not shown) or a control unit (not shown). The electric circuit 30 may be integrated in an electromagnetic field transmitter (source).

Figure 4C:
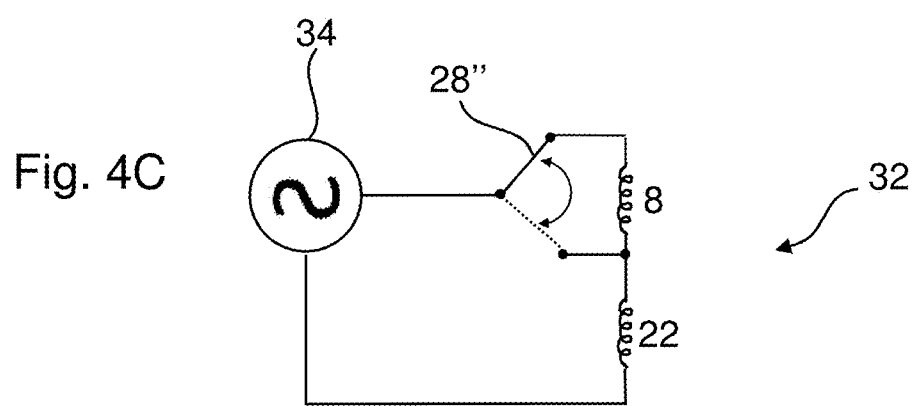
FIG. 4C shows a further electric circuit of an electromagnetic tracking system according to the invention.

FIG. 4C illustrates an electric circuit 32 of an electromagnetic tracking system according to the invention. The electric circuit 32 comprises an AC generator 34 arranged to provide a first inductor (a coil of the source of the system) 22 and an offset coil 8 that is arranged in series with the first coil 22. A switch (e.g. a transistor) 28" is arranged to electrically connect either only the first coil 22 or both the first coil 22 and the offset coil 8 by means of a switch 28". Accordingly, the additional coil (offset coil) 8 can be activated and deactivated using the switch 28" that may be controlled by using a processor or a control unit (not shown). The electric circuit 32 may be integrated in a source.

Figure 5A:
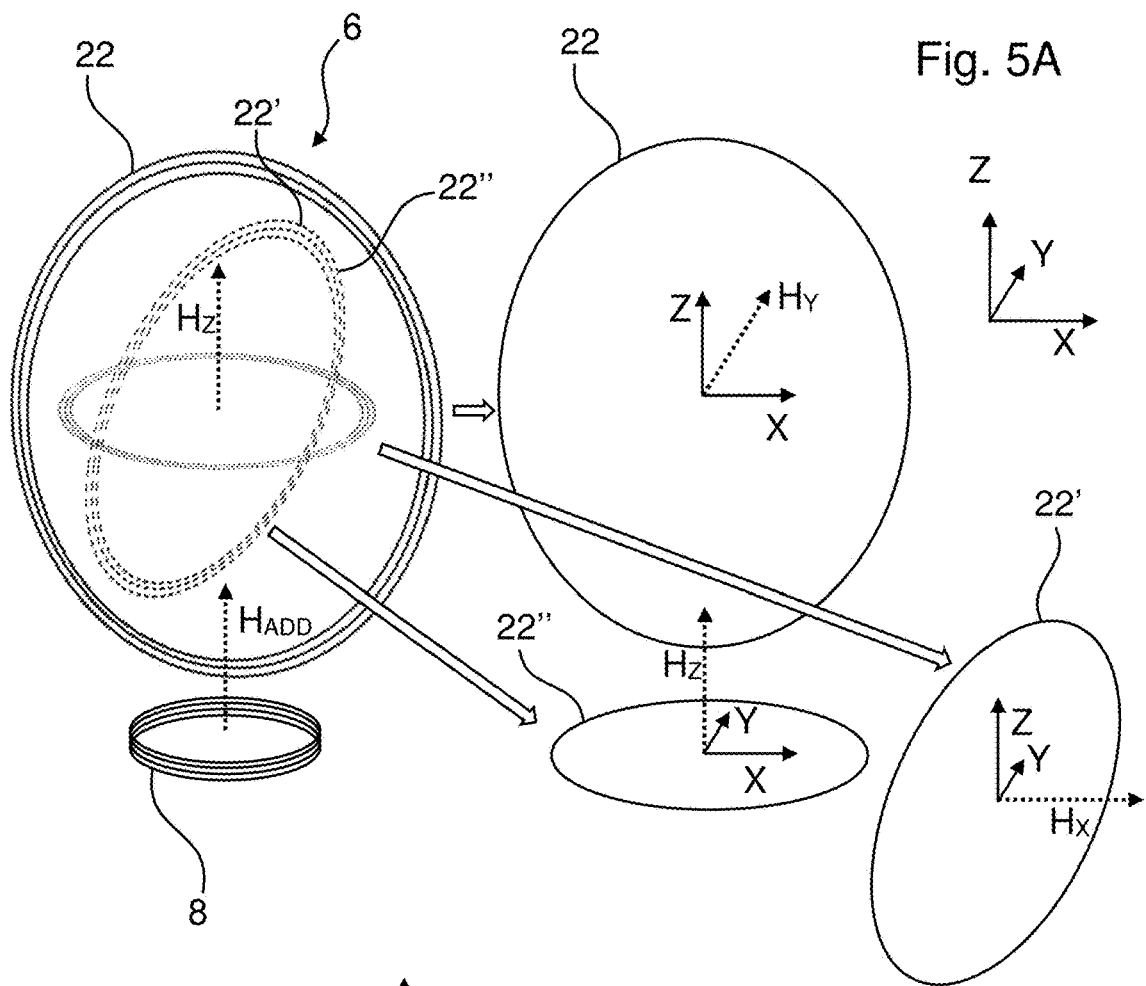
FIG. 5A shows a schematic view of an electromagnetic field transmitter comprising an offset coil arranged to generate an additional magnetic field.

FIG. 5A illustrates a schematic view of an electromagnetic field transmitter comprising a coil assembly 6 and a single offset coil 8 arranged to generate an additional magnetic field $H_{ADD}$. The coil assembly 6 comprises three orthogonal coils 22, 22', 22" configured to generate three magnetic fields $H_x$, $H_y$, $H_z$.

Each of the coils 22, 22', 22" of the coil assembly 6 are schematically shown at the right side of the coil assembly 6. The magnetic fields $H_x$, $H_y$, $H_z$ generated by each coil 22, 22', 22' as well as the orientation of the coils 22, 22', 22'" relative to the three axes X, Y, Z are shown as well. In FIG. 5A it can be seen that the first coil 22" extends in the plane spanned by the X-axis and the Y-axis and that the magnetic field $H_Z$ generated by this coil 22" extends along the Z-axis. It can be seen that the second coil 22' extends in the plane spanned by the Y-axis and the Z-axis and that the magnetic field $H_X$ generated by this coil 22' extends along the X-axis. The third coil 22 extends in the plane spanned by the X-axis and the Z-axis and that the magnetic field $H_Y$ generated by this coil 22 extends along the Y-axis.

In FIG. 5A, the first coil 22", is smaller than the second coil 22' that is smaller than the third coil 22. The coils 22, 22', 22" have a circular configuration. However, as shown in FIG. 5B, the geometry of the coils may be different.

Figure 5B:
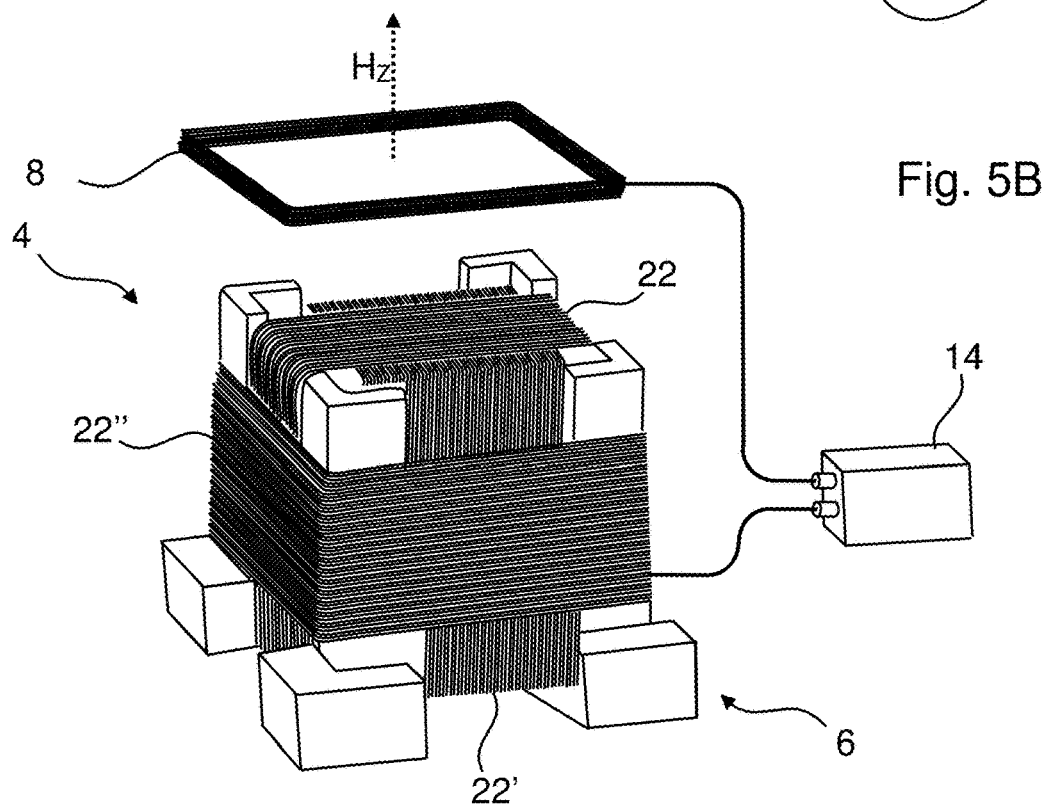
FIG. 5B shows a schematic perspective view of another electromagnetic field transmitter that comprises an offset coil arranged to generate an additional magnetic field.

FIG. 5B illustrates a schematic perspective view of an electromagnetic tracking system comprises a differently shaped electromagnetic field transmitter 4 comprising a coil assembly 6 and an offset coil 8 arranged to generate an additional magnetic field $H_Z$. The coil assembly 6 comprises three orthogonal coils 22, 22', 22" wound on a cubic core. The electromagnetic tracking system comprises a control unit 14 electrically connected to the coils 22, 22', 22" and to the offset coil 8. The control unit 14 is configured to electrically energize the coils 22, 22', 22".

In an embodiment, the control unit 14 is electrically connected to a switch (not shown) arranged to connect and disconnect a first point of the offset coil 8 to a second point of the offset coil 8, wherein the offset coil 8 is configured to generate the additional magnetic field $H_Z$ (by induction) when the first point of the offset coil 8 and the second point of the offset coil 8 are electrically connected to each other by means of the switch. The offset coil 8 is restricted from generating the additional magnetic field $H_Z$ when the first point of the offset coil 8 and the second point of the offset coil 8 are electrically disconnected from each other by means of the switch.

In another embodiment, the control unit 14 is configured to deliver an AC current to the offset coil 8 in order to generate the additional magnetic field $H_Z$.

The offset coil 8 is configured to generate the additional magnetic field $H_Z$ in order to carry out the calibration process of the invention. In practice, the offset coil 8 may be placed in another position, e.g. be integrated in the coil assembly 6 or be arranged in a PCB (not shown) to which the coil assembly 6 is attached and electrically connected.

FIG. 6A illustrates the measured voltage U graphically as a function of time T, wherein a sensor 12 is arranged in a first configuration. The graph 36 showing the voltage U has the form of a sine wave. The sensor 12 is arranged in a configuration, in which the top portion 14 of the sensor 12 is white, wherein the bottom portion 14' is dark. Instead of depicting the measured voltage U as function of time T, it would be possible to depict the measured current as function of time T.

FIG. 6B illustrates the measured voltage U graphically as function of time T in a configuration, in which the sensor 12 is arranged in a second configuration. In this configuration the top portion 14 of the sensor 12 is dark, wherein the bottom portion 14' is white. Accordingly, compared to FIG. 6A, the sensor 12 has been turned upside down.

In FIG. 6A and FIG. 6B, the position of the sensor 12 can be detected. The orientation, however, is not uniquely determined. Therefore, the calibration method according to the invention (e.g. explained with reference to FIG. 3) can be used to determine the orientation of the sensor 12.

FIG. 6C and FIG. 6D illustrate how PSK is used to gain additional information for carrying out the method according to the invention. Voltage is plotted against time T. In FIG. 6C, the uppermost part of the graph shows a first sine signal 38 (carrier wave illustrated with a dotted line) and a modulated sine signal 40 (illustrated with a solid line) generated by using the control unit (not shown) of the electromagnetic tracking system. Eight periods of the carrier wave 38 are illustrated above a single period of the PSK modulated signal 40. As indicated with small arrows pointing upwards both the carrier wave 38 and the PSK modulated signal 40 have a positive derivative. This indicates that the carrier wave 38 and the PSK modulated signal 40 are in phase at time T=0.

In FIG. 6D, the uppermost part of the graph shows a first sine signal 38' (carrier wave illustrated with a dotted line) and a modulated sine signal 40' (illustrated with a solid line) generated by using the control unit of the electromagnetic tracking system. Eight periods of the carrier wave 38' are illustrated above a single period of the PSK modulated signal 40'.

The small arrows indicate that the carrier wave 38 has a negative derivative and that the PSK modulated signal 40 has a positive derivative. As the arrows point in different directions, this indicates that the carrier wave 38 and the PSK modulated signal 40 are 180° out of phase at time T=0.

LIST OF REFERENCE NUMERALS

2 Electromagnetic tracking system
4 Electromagnetic field transmitter
6 Coil assembly
8, 8', 8" Offset coil
10 Printed circuit board (PCB)
12 Electromagnetic field receiver (sensor)
14 Top portion
14' Bottom portion
16 Hemisphere system 18 South hemisphere
18' North hemisphere
20 Electrical circuit
22, 22', 22" Coil
24 Current generator
26 Current impulse
28, 28', 28" Switch
30, 32 Electrical circuit
34 AC generator
36, 36' Measured voltage
38, 38', 40 Sine signal
42 Sine signal
44 Separation line
46 Control unit
48 Connector
$\vec{N}$ First vector
$\vec{S}$ Second vector
X, Y, Z Axis
$H_X$, $H_Y$, $H_Z$ Magnetic field
$H_{ADD}$ Additional magnetic field
$C_1$, $C_2$ Capacitor
$L_1$, $L_2$ Coil
U Voltage
T, $T_1$ Time

What is claimed is:

1. A three-dimensional alternating current electromagnetic field tracking system for determining the position and orientation of an object, wherein the tracking system comprises:
    an electromagnetic field transmitter comprising three coils configured to generate three magnetic fields;
    one or more electromagnetic field receivers (sensors) each comprising three measurement coils; and
    a control unit,
    wherein the tracking system is configured to carry out a digital modulation process to determine one or more parameters needed for calibration, wherein the digital modulation process is a phase-shift keying (PSK) modulation process modulating a phase of a constant frequency carrier wave, wherein the tracking system is configured to determine if the constant frequency carrier wave and the phase modulated signal are in-phase or 180° out-of-phase at time T=0, thereby determining an operational sign of the constant frequency carrier wave and thus the orientation of the one or more sensors.

2. The tracking system according to claim 1, wherein the electromagnetic field transmitter comprises at least one offset coil arranged to generate an additional magnetic field, wherein the offset coil is offset relative to the coils of the electromagnetic field transmitter.

3. The tracking system according to claim 2, wherein the control unit is configured to calibrate the tracking system on the basis of the additional magnetic field ($H_{add}$).

4. The tracking system according to claim 2, wherein the at least one offset coil is arranged and configured to generate the additional magnetic field passively by induction.

5. The tracking system according to claim 2, wherein the at least one offset coil comprises a switch connected to the control unit, wherein the switch is configured to connect and disconnect a first point of the offset coil to a second point of the offset coil.

6. The tracking system according to claim 5, wherein the offset coil is configured to generate the additional magnetic field by induction when the first point of the offset coil and the second point of the offset coil are electrically connected to each other by the switch and wherein the offset coil is restricted from generating the additional magnetic field by induction when the first point of the offset coil and the second point of the offset coil are electrically disconnected from each other by the switch.

7. The tracking system according to claim 2, wherein the at least one offset coil is arranged in a configuration in which the additional magnetic field generated by the at least one offset coil extends parallel to one of the three magnetic fields generated by one of the coils of the electromagnetic field transmitter.

8. The tracking system according to claim 2, wherein the electromagnetic field transmitter is arranged on a printed circuit board (PCB).

9. The tracking system according to claim 8, wherein the at least one offset coil is integrated in the PCB.

10. The tracking system according to claim 8, wherein the at least one offset coil extends in a plane perpendicular to the plane of the PCB.

11. A method for automatic calibration of a three-dimensional alternating current electromagnetic field tracking system comprising an electromagnetic field transmitter comprising three coils configured to generate three magnetic fields, one or more electromagnetic field receivers each comprising three measurement coils, and a control unit, the method comprising:
    carrying out a digital modulation process to determine one or more parameters needed for calibration, wherein the digital modulation process is a phase-shift keying (PSK) modulation process modulating a phase of a constant frequency carrier wave; and
    determining if the constant frequency carrier wave and the phase modulated signal are in-phase or 180° out-of-phase at time T=0, thereby determining an operational sign of the constant frequency carrier wave and thus the orientation of the one or more sensors.

12. The method according to claim 11 further comprising generating an additional magnetic field from an offset coil being offset relative to the coils of the electromagnetic field transmitter.

13. The method according to claim 12 further comprising calibrating the tracking system on the basis of the additional magnetic field.

14. The method according to claim 12, wherein the offset coil is arranged and configured to generate the additional magnetic field passively by induction.

15. The method according to claim 12, wherein the additional magnetic field is generated using at least one offset coil that is arranged in a configuration in which the additional magnetic field generated by the at least one offset coil extends parallel to one of the three magnetic fields generated by one of the coils of the electromagnetic field transmitter.

16. The method according to claim 11, wherein the method is carried out using a control unit that is integrated in the electromagnetic field transmitter.

17. The method according to claim 16 further comprising connecting and disconnecting a first point of the offset coil to a second point of the offset coil with a switch.

18. The method according to claim 12, wherein the additional magnetic field generated by the at least one offset coil extends parallel to one of the three magnetic fields generated by one of the coils of the electromagnetic field transmitter.

19. The method according to claim 11, wherein the electromagnetic field transmitter is arranged on a printed circuit board (PCB).

20. The method according to claim 19, wherein the at least one offset coil is integrated in the PCB or the at least one offset coil extends in a plane perpendicular to the plane of the PCB.

\* \* \* \* \*